United States Patent [19]

Bombardelli et al.

[11] Patent Number: 5,264,216

[45] Date of Patent: Nov. 23, 1993

[54] PHARMACEUTICAL USES OF BILOBALIDE AND DERIVATIVES THEREOF AND PHARMACEUTICAL COMPOSITIONS ADAPTED FOR SUCH USE

[75] Inventors: Ezio Bombardelli; Mario Ghione, both of Milan, Italy

[73] Assignee: Indena SpA, Milan, Italy

[21] Appl. No.: 857,220

[22] Filed: Mar. 25, 1992

[30] Foreign Application Priority Data

Feb. 13, 1992 [GB] United Kingdom ................ 9202993

[51] Int. Cl.$^5$ .............................................. A61K 9/02
[52] U.S. Cl. ...................................... 424/433; 424/49; 424/450; 514/78; 514/463; 514/944; 514/967
[58] Field of Search ............ 424/433, 434, 435, 195.1, 424/49, 450; 514/78, 944, 967, 463

[56] References Cited

U.S. PATENT DOCUMENTS 4,892,883  1/1990  Chattarjee et al. ................ 514/464

*Primary Examiner*—Thurman K. Page
*Assistant Examiner*—Jyothsna Venkat
*Attorney, Agent, or Firm*—Kirschstein, Ottinger, Israel & Schiffmiller

[57] ABSTRACT

A method of treating an infection in an individual, by administering an effective dose of bilobalide or of a pharmacologically acceptable derivative thereof. Activity against infection with *Pneumocystis carinii* has major utility in treating AIDS-associated infections. Bilobalide may be administered systemically or topically in accordance with the invention. For systemic use, oral and parenteral routes of administration may be used.

15 Claims, No Drawings

PHARMACEUTICAL USES OF BILOBALIDE AND DERIVATIVES THEREOF AND PHARMACEUTICAL COMPOSITIONS ADAPTED FOR SUCH USE

BACKGROUND OF THE INVENTION

1. Field of the Invention

This invention relates to novel pharmaceutical uses of bilobalide and derivatives thereof, and to pharmaceutical compositions adapted for such use.

2. Description of Related Art

Bilobalide is a sesquiterpene of formula

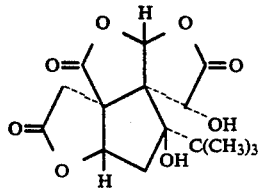

which may be extracted from leaves of the tree *Ginkgo biloba*.

Bilobalide was first isolated from the leaves of *Ginkgo biloba* and chemically analysed in 1969 (K. Weinges, Liebigs Ann. Chem. (1969) 724, 214 and K. Nakanisshi, J. Am. Chem. Soc., (1971) 93, 3544).

Recently various medical applications have been proposed for bilobalide in the treatment of pathological conditions of the nervous system. For example U.S. Pat. No. 4,892,883 and EP-A-0 143 977 describe the pharmacological use of bilobalide in the treatment of neuropathies, inflammatory conditions and immunodeficient and neurological conditions of traumatic origin. EP-A-0 441 279 describes the use of bilobalide derivatives, particularly complexes with phospholipids, in the treatment of peripheral disorders associated with inflammatory and neurodystrophic alterations.

No other useful biological effects have been reported and, in fact, EP-A-0 143 977 specifically states that bilobalide has no antifungal action against *Monilia fructicola* or *Penicillium glaucum* and no antibacterial action against *Escherichia coli*.

It is thus extremely surprising that following an extensive investigation of the biological properties of bilobalide, it has been found that bilobalide and derivatives thereof may be used in the treatment of infections with pathological strains of a variety of diverse pathogenic bacterial, fungal and protozoal organisms.

SUMMARY OF THE INVENTION

Thus according to one aspect of the present invention there is provided a method of treating an infection in an individual, which comprises administering to the individual via a route of administration which delivers it to the site of infection, an effective dose of bilobalide or of a pharmacologically acceptable derivative thereof. Bilobalide may be administered systemically or topically in accordance with the invention. For systemic use, oral and parenteral routes of administration may be used.

The invention further provides the use of bilobalide or of a pharmacologically acceptable derivative thereof in the manufacture of a pharmaceutical composition for treating an infection in an individual.

Thus in the course of an extensive screening program it has surprisingly been found that bilobalide and derivatives thereof are active in vitro against colonies of pathological strains of organisms including *Trichomonas vaginalis, Staphylococcus aureus, Streptococcus faecalis, Escherichia coli*, Lactobacillus sp., *Pneumocystis carinii* and that useful in vivo antibiotic activity has also been observed.

In view of these activities, bilobalide and pharmacologically acceptable derivatives thereof provide valuable therapeutic agents for use where existing treatments are ineffective, non-existent, or associated with undesirable side-effects.

Thus for example bilobalide has been found to be active against *Trichomonas vaginalis*. Although the action of bilobalide on *Trichomonas vaginalis* is less powerful than that of the 5-nitro-imidazole derivatives (highly potent drugs used against *T vaginalis* and other protozoa) the latter suffer the disadvantage of being poorly tolerated by some individuals who can display allergic reactions to the known drugs. The use of bilobalide to treat such patients enables the problem of sensitivity to 5-nitro-imidazole derivatives to be avoided. A further factor rendering bilobalide worthy of investigation is its action on Lactobacillus sp.

Bilobalide has in fact proved to be very effective in reducing infections caused by these parasites in the vaginal milieu, where lactobacilli and flagellates form part of the biocenosis and also in the teatment of periodontal infections. It it is also extremely well tolerated.

Thus according to a further, more specific aspect of the present invention there is provided a method of treating a vaginal infection in an individual, which comprises administering an effective dose of bilobalide or of a pharmacologically acceptable derivative thereof to the vagina.

The invention further provides the use of bilobalide or of a pharmacologically acceptable derivative thereof in the manufacture of a pharmaceutical composition for treating a vaginal infection in an individual. For such applications, the bilobalide or a pharmacologically acceptable derivative thereof is conveniently administered in the form of a pessary or vaginal suppository, or as a cream or gel adapted for vaginal administration.

According to a further aspect of the present invention there is provided a method of treating a periodontal infection in an individual, which comprises administering an effective dose of bilobalide or of a pharmacologically acceptable derivative thereof to the mouth. In this embodiment the invention further provides the use of bilobalide or of a pharmacologically acceptable derivative thereof in the manufacture of a pharmaceutical composition for treating a periodontal infection in an individual. For such applications, the bilobalide or a pharmacologically acceptable derivative thereof is conveniently administered in the form of a toothpaste, mouth-wash or other orally acceptable composition.

Bilobalide and pharmacologically acceptable derivatives thereof has also been found to exhibit an antibiotic effect against *Pneumocystis carinii*, a microorganism which is the causative organism of pneumonia in immunologically impaired individuals.

*Pneumocystis carinii* is a microorganism the taxonomic classification of which causes some disagreement (most sources classifying it as a protozoon, but some classify it as a fungus). *Pneumocystis carinii* is known to be responsible for fatal cases of pneumonia in patients exhibiting immuno-suppression, particularly patients infected with HIV and exhibiting to a greater or lesser extent, the symptoms associated with AIDS. The activity of bilobalide against this organsim thus makes it a promising drug for treating AIDS sufferers, thus making its use of highly topical significance.

The recently introduced culture of this parasite is helping the study of new drugs and comparisons with existing drugs. In our experiments bilobalide was compared with cotrimoxazole, over which it has valuable therapeutic advantages. In vitro, in concentrations exceeding 12 μg/ml (active concentration), bilobalide exerts an effect equal to the reference substance, but in higher doses its effect is definitively superior, indicating that the dose-effect curve is not parallel but superior to that of cotrimoxazole. In vivo the maximum dose of bilobalide that can be tolerated is 100 mg/kg for 5 days i.p.. A dose of 10 mg/kg is well tolerated and significantly reduces disease in experimental animals.

Thus according to a further aspect of the present invention there is provided a method of treating an infection in an individual with Pneumocystis carinii, which comprises administering an effective dose of bilobalide or of a pharmacologically acceptable derivative thereof.

The invention further provides the use of bilobalide or of a pharmacologically acceptable derivative thereof in the manufacture of a pharmaceutical composition for treating a pulmonary infection in an individual, especially an individual suffering an infection with Pneumocystis carinii.

DETAILED DESCRIPTION OF THE PREFERRED EXAMPLES

Examples of pharmacologically acceptable derivatives of bibobalide which may be used in accordance with the invention are esters, for example esters in which one or both of the hydroxy groups of bilobalide are esterified with an acid such as a $C_{2\text{-}22}$ carboxylic acid. Such esters include esters with $C_{2\text{-}22}$ alkanoic acids, $C_{2\text{-}22}$ alkenoic acids and $C_{2\text{-}22}$ alkadienoic acids. Such acids have the formulae $C_nH_{2n+1}COOH$, $C_nH_{2n-1}COOH$ and $C_nH_{2n-3}COOH$ (n=1-21, especially 17-21).

Other derivatives include complexes with phospholipids. Such complexes include compounds having the general formula

```
CH2—O—R
|
CH—O—R1
|           O-
|          /
CH2—O—P
        ‖\
        O  O—R2+
``` wherein R and $R_1$, which can be the same or different are each an acyl residue of a $C_{16\text{-}22}$ saturated or unsaturated fatty acid, and $R_2$ is $-CH_2CH_2N(CH_3)_3$, $-CH_2CH_2NH_2$, $-CH_2CH_2(COOH)NH_2$

PHARMACOLOGICAL DATA

Bilobalide was subjected to the following tests:

1. In vitro Tests on Schizomycetes

Solutions of the substance in varying dilutions were added in equal parts to agarized Mueller-Hinton culture medium kept in a liquid state at 56° C., then poured into Petri dishes. After solidification, the dishes were surface sown with suspensions of schizomycetes recently isolated from pathological materials and incubated at 37° C. in an atmosphere of $CO_2$ for 18 hours.

1.1. Tests on Protozoa 1.1.1 *Trichomas vaginalis*

Suspensions of the protozoom from cultures in Brain Heart Infusion Broth with 5% horse serum of material recently isolated from human pathological samples were distributed in portions of 200 μl/well in plastic plates with 20 wells containing bilobalide in scalar concentrations in physiological saline.

The motility and multiplication of the protozoa were assessed from observation under an inverted microscope after various periods of incubation at 37° C. in an atmosphere of $CO_2$.

1.1.2 *Pneumocystis carinii*

Suspensions of the microorganism obtained from homogenised infected lung tissue were prepared in Minimal Medium (Eagle modf.) to which were added a solution of non-essential amino acids, 5% calf fetus serum and antibiotics. These solutions were sown onto cultures of HEL 229 fetal lung cells treated with solutions of the substance in MEM in varying concentrations.

After being incubated for various periods at 37° C. in an atmosphere containing 5% $CO_2$, the cultures were fixed in methanol, stained with Giemsa and examined under the microscope to determine the parasite count. In this case, parallel tests were carried out with cotrimoxazole, the reference drug for tests on this microorganism.

2. In vivo Tests—*Pneumocystis carinii*

In vivo tests were conducted in rats treated with cortisone and infected pertracheally with suspensions of *Pneumocystis carinii*, which received 10-100 mg/kg bilobalide for 5 days. These doses were selected on the basis of pharmacokinetic and toxicological data. Other groups were treated with cotrimoxazole and others kept as controls.

The surviving animals were sacrificed at the end of a subsequent observation period and the lungs examined for the presence of the parasite.

The table below gives some of the data on the inhibitory effect on the growth of various schizomycetes:

3. In vitro Tests 3.1. Effect of bilobalide on various schizomycetes

|  | Concentrations μg/ml | | | | |
| --- | --- | --- | --- | --- | --- |
| Strains | 0 | 0.1 | 1 | 10 | 100 |
| Staphylococcus aureaus | +++ | +++ | +++ | ++ | — |
| Streptococcus faecalis | +++ | ++ | + | ++ | — |
| Lactobacillus sp | ± | + | = | — | — |
| Pseudomanas aeruginosa | ++ | + | ± | — | — |

+ = growth
− = no growth 3.2 Effect of bilobalide on Trichomonas vaginalis

| Result after | Concentrations μg/ml | | | | | | | | | | |
|---|---|---|---|---|---|---|---|---|---|---|---|
| | 0 | | 0.05 | | 0.5 | | 5 | | 50 | | 500 |
| | A | B | A | B | A | B | A | B | A | B | A | B |
| 10' | +++ | +++ | +++ | +++ | +++ | +++ | ++ | +++ | ++ | +++ | + | +++ |
| 180' | +++ | +++ | +++ | +++ | +++ | +++ | ++ | +++ | ++ | +++ | + | +++ |
| 18 h | +++ | +++ | + | ++ | + | + | ± | ± | − | ± | − | − |
| 50 h | +++ | +++ | + | ++ | ± | ± | ± | − | − | − | − | − |

A = mobility (+++ = normal, − = absent)
B = morphology (+++ = normal, − = significantly altered)

3.3 In vitro effect of bilobalide on Pneumocystis carinii

| Days' incubation | Concentrations μg/ml | | | | | | | | | |
|---|---|---|---|---|---|---|---|---|---|---|
| | 0 | | 6.3 | | 12.5 | | 25 | | 500 | |
| | A | B | A | B | A | B | A | B | A | B |
| 1 | + | + | + | + | + | + | + | + | + | + |
| 5 | ++ | ++ | ++ | ++ | + | + | + | − | + | + |
| 8 | ++ | ++ | + | + | + | − | + | − | + | + |

A = bilobalide
B = cotrimoxazole

4. In vivo Effect of Bilobalide on *Pneumocystis carinii* after Intraperitoneal Administration

| | Dose in mg/Kg d × 5 | | | | | |
|---|---|---|---|---|---|---|
| | 0 | | 10 | | 100 | |
| | A | B | A | B | A | B |
| biblobalide | 10 | 100 | 0 | 100 | 0 | 5 |
| cotrimoxazole | 10 | 100 | 10 | 100 | 0 | 10 |

A = mortality, %
B = pulmonary lesions, %

Bilobalide has proved effective in man in doses of between 1 and 100 mg/kg.

Regarding other diseases of fungal or protozoal origin, bilobalide has proved effective in periodontal diseases of unknown origin that were resistant to conventional treatments based on antibiotics and antifungal agents.

For systemic treatment in animals and man, complexes of bilobalide with phospholipids already described in patent application (EP-0 441 279) have been found to be particularly effective since they exhibit greater bioavailability than the product in its free form. Complexes with distearoyl phosphatidyl choline or natural phosphatidyl choline extracted from soya are of particular value.

Bilobalide and its complexes can be incorporated in standard pharmaceutical formulations: ampoules, hard and soft gelatine capsules, tablets, suppositories, vaginal pessaries, creams and ointments. Bilobalide or its related complexes can be used in treating a wide range of infections, alone and in combination therapies with other antibiotics.

Bilobalide may be formulated with conventional excipients and carriers, particularly those adapted for administration in the milieux specifically referred to herein. Specific examples of pharmaceutical formulations, and excipients and preservatives may be found in standard textbooks of pharmacology, e.g. Remington, etc.

We claim:

1. A method of combatting an infection in an individual having an infection with a pathological strain selected from the group consisting of *Trichomonas vaginalis, Staphylococcus aureus, Streptococcus faecalis, Escherichia coli*, Lactobacillus sp. and *Pneumocystis carinii*, which comprises administering to the individual via a route of administration which delivers it to the site of infection, an effective dose of bilobalide or of a pharmacologically acceptable derivative thereof, whereby an antibiotic effect against said pathological strain is obtained.

2. A method according to claim 1 wherein said pharmacologically acceptable derivatives are esters in which one or both of the hydroxy groups of bilobalide are esterified with a $C_{2-22}$ carboxylic acid.

3. A method according to claim 2 wherein the $C_{2-22}$ carboxylic acids are selected from $C_{2-22}$ alkanoic acids, $C_{2-22}$ alkenoic acids and $C_{2-22}$ alkadienoic acids having the formulae $C_nH_{2n+1}COOH$, $C_nH_{2n-1}COOH$ and $C_nH_{2n-3}COOH$ (n=1-21), respectively.

4. A method according to claim 13 wherein n is from 17 to 21.

5. A method according to claim 1 wherein said pharmacologically acceptable derivatives are complexes of bilobalide with phospholipids.

6. A method according to claim 5 wherein said complexes have the formula $$\begin{bmatrix} CH_2-O-R \\ CH-O-R_1 \\ CH_2-O-P\begin{smallmatrix}O^-\\ \\ \|\\O\end{smallmatrix}O-R_2^+ \end{bmatrix}$$

wherein R and $R_1$, which can be the same or different are each an acyl residue of a $C_{16-22}$ saturated or unsaturated fatty acid, and $R_2$ is $-CH_2CH_2N(CH_3)_3$, $-CH_2CH_2NH_3$ or $-CH_2CH_2(COOH)NH_3$.

7. A method of treating a vaginal infection in an individual, which comprises administering an effective dose of bilobalide or of a pharmacologically acceptable derivative thereof to the vagina.

8. A method according to claim 7 wherein said pharmacologically acceptable derivatives are esters in which one or both of the hydroxy groups of bilobalide are esterified with a $C_{2-22}$ carboxylic acid.

9. A method according to claim 8 wherein the $C_{2-22}$ carboxylic acids are selected from $C_{2-22}$ alkanoic acids, $C_{2-22}$ alkenoic acids and $C_{2-22}$ alkadienoic acids having the formulae $C_nH_{2n+1}COOH$, $C_nH_{2n-1}COOH$ and $C_nH_{2n-3}COOH$ (n=1-21), respectively.

10. A method according to claim 9 wherein n is from 17 to 21.

11. A method according to claim 10 wherein said pharmacologically acceptable derivatives are complexes of bilobalide with phospholipids.

12. A method according to claim 11 wherein said complexes have the formula

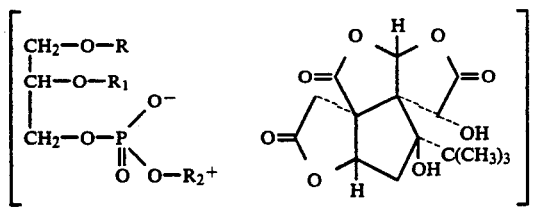

wherein R and $R_1$, which can be the same or different are each an acyl residue of a $C_{16-22}$ saturated or unsaturated fatty acid, and $R_2$ is $-CH_2CH_2N(CH_3)_3$, $-CH_2CH_2NH_2$ or $-CH_2CH_2(COOH)NH_2$.

13. A method according to claim 1 wherein said infection is with an individual with *Pneumocystis carinii*, which comprises administering an effective dose of bilobalide or of a pharmacologically acceptable derivative thereof.

14. A pharmaceutical composition for combatting a vaginal infection in an individual having a vaginal infection with a pathological strain selected from the group consisting of *Trichomonas vaginalis, Staphylococcus aureus, Streptococcus faecalis, Escherichia coli*, Lactobacillus sp. and *Pneumocystis carinii* which comprises bilobalide or a pharmacologically acceptable derivative thereof and a pharmceutically acceptable excipient, said composition being in a form adapted for vaginal administration.

15. A pharmaceutical composition according to claim 14 being in the form of a vaginal suppository.

* * * * *